(12) United States Patent
Kang et al.

(10) Patent No.: US 8,084,062 B2
(45) Date of Patent: Dec. 27, 2011

(54) ANTI-AGING COSMETIC COMPOSITION

(75) Inventors: Chan Koo Kang, Gyeonggi-do (KR); Young Jin Lee, Gyeonggi-do (KR); Sang Hoon Han, Gyeonggi-do (KR); Seung Hun Kim, Seoul (KR)

(73) Assignee: Amorepacific Corporation, Seoul (KR)

( * ) Notice: Subject to any disclaimer, the term of this patent is extended or adjusted under 35 U.S.C. 154(b) by 50 days.

(21) Appl. No.: 12/654,635

(22) Filed: Dec. 28, 2009

(65) Prior Publication Data

US 2010/0119628 A1 May 13, 2010

Related U.S. Application Data

(62) Division of application No. 11/795,875, filed as application No. PCT/KR2005/003770 on Nov. 8, 2005, now abandoned.

(30) Foreign Application Priority Data

Jan. 31, 2005 (KR) .................. 10-2005-0008665

(51) Int. Cl.
*A61K 36/00* (2006.01)
*A61K 36/48* (2006.01)

(52) U.S. Cl. ........................ 424/725; 424/757

(58) Field of Classification Search .................. None
See application file for complete search history.

(56) References Cited

U.S. PATENT DOCUMENTS

| | | | |
|---|---|---|---|
| 5,100,879 A * | 3/1992 | Ueno et al. ............ 514/59 |
| 5,939,082 A | 8/1999 | Oblong et al. | |
| 6,379,719 B1 | 4/2002 | Gilles | |
| 6,682,763 B2 | 1/2004 | Kuno et al. | |
| 7,547,454 B2 * | 6/2009 | Gupta ............ 424/642 |
| 2003/0224028 A1 | 12/2003 | Galey | |
| 2004/0208902 A1 | 10/2004 | Gupta | |
| 2006/0045896 A1 | 3/2006 | Morariu | |
| 2006/0074108 A1 * | 4/2006 | Gupta ............ 514/332 |
| 2006/0110415 A1 * | 5/2006 | Gupta ............ 424/401 |
| 2006/0216251 A1 | 9/2006 | Morariu | |
| 2007/0166255 A1 * | 7/2007 | Gupta ............ 424/70.1 |
| 2008/0268077 A1 * | 10/2008 | Vielhaber ............ 424/756 |

FOREIGN PATENT DOCUMENTS

KR 2001057429 7/2001

OTHER PUBLICATIONS

International Search Report mailed Mar. 7, 2006.
Liu CL et al.: "In vivo protective effect of protocatechuic acid on tert-butyl hydroperoxide-induced rat hepatotoxicity," in Food Chem Toxicol, May 2002, vol. 40, No. 5, pp. 635-641.
Herrera-Arellano et al.: "Effectiveness and tolerability of a standardized extract from *Hibiscus sabdariffa* in patients with mild to moderate hypertension: a controlled and randomized clinical trial," in Phytomedicine, Jul. 2004, vol. 11, No. 5, pp. 375-382.
Sharma et al.: "Effect of Hibiscus rosa sinensis extract on hyperproliferation and oxidative damage caused by benzoyl peroxide and ultraviolet radiations in mouse skin," in Basic Clin Pharmacol Toxicol 2004, Nov. 2004, vol. 95, No. 5, pp. 220-225.
Official Action and English translation of Chinese Office Action dated Aug. 21, 2009.
Internet Press Room article on MYOXINOL by Cogins, dated Feb. 24, 2004, 3 pages, from www.cognis.com.

* cited by examiner

*Primary Examiner* — Christopher R. Tate
(74) *Attorney, Agent, or Firm* — Nixon & Vanderhye P.C.

(57) ABSTRACT

The present invention relates to an anti-aging cosmetic composition, and more particularly, the present invention relates to an anti-aging cosmetic composition containing *Hibiscus esculentus* extracts and at least one selected from the group consisting of oleanolic acid, ursolic acid, glycyrhetinic acid and retinol, showing high safety to skin and wrinkle-improvement effect.

4 Claims, 1 Drawing Sheet

ANTI-AGING COSMETIC COMPOSITION

This application is a divisional of application Ser. No. 11/795,875 filed Nov. 20, 2007 now abandoned, which in turn is the U.S. national phase of International Application No. PCT/KR2005/003770 filed 8 Nov. 2005 which designated the U.S. and claims priority to KR 10-2005-0008665 filed 31 Jan. 2005, the entire contents of each of which are hereby incorporated by reference.

TECHNICAL FIELD

The present invention relates to an anti-aging cosmetic composition, and more particularly to an anti-aging cosmetic composition showing superior safety to skin and skin-wrinkle improvement, containing *Hibiscus esculentus* extracts and at least one selected from the group consisting of oleanolic acid, ursolic acid, glycyrrhetinic acid and retinol.

BACKGROUND ART

Human skin, as a primary protective barrier, protects the vital organs of the body from external irritants such as changes in temperature and humidity, ultraviolet rays and contaminants, and plays an important role in the regulation of biological homeostasis such as thermoregulation. However, as skin ages, it shows skin aging effects such as loss of elasticity, keratinization, formation of skin wrinkles and skin contraction. The cause of this skin aging can be classified as internal factors such as cell gene transformation and cell tissue change, and external factors such as UV and humidity (Masamitsu Ichihashi, Fragrance Journal, Vol. 32, No. 5, 24-30). In particular, skin aging effect due to UV is called "photoaging". In photoaging, oxygen free radicals are generated in cells by UV light, and the oxygen free radicals accelerate the synthesis of protease (MMP-1, MMP-3, MMP-9, etc.), enzyme that decomposes protein such as collagen or elastin that is elasticity fiber of derma, by way of the signal transduction system raising an inflammation reaction, and thereby decreasing the elasticity of derma and producing the skin wrinkle.

Therefore, in order to prevent skin aging and keep more healthy and elastic skin, studies have been made to develop physiological active substances having a skin wrinkle improvement effect. For example, in 1995, trans-retinoic acid was approved by FDA as a therapeutic for the improvement of photoaged skin. In addition, retinol, which has fewer side effects, has been used in cosmetics since the mid 1990's, and various cosmetics for skin wrinkle improvement have appeared on the market. Since then, female hormonally active agents or antioxidants extracted from various plants have been introduced to cosmetics as skin wrinkle improving agents.

However, most of the above agents have many problems such as weak efficacy or serious side effects. Thus, extensive studies have been undertaken on substances having an anti-aging effect with no side effects. Among these, there has been much attention on peptides, which have various biological activities, as novel ingredients of highly functional cosmetics. Peptides are biopolymer having 20 essential amino acids linked via amide bond, and it has been expected that peptides would produce direct effects on in vivo metabolism due to their great interaction with protein.

Korean Laid-Open Publication No. 2001-0006358 discloses a cosmetic composition containing protein fraction extracted from the seed of *Hibiscus esculentus*. Examples are disclosed regarding a process for extracting protein fractions from *Hibiscus esculentus* and a cosmetic composition containing the protein fraction; however, no use is disclosed of the cosmetic composition containing extracts of *Hibiscus esculentus* for anti-aging.

Recently, much attention has been paid to the treatment of "expression wrinkle," which is generated by mechanical movement of facial muscle, as well as to the treatment of endogenous aging generated by aging and of photoaging generated by UV light. With regard to the improvement of expression wrinkle, botulic toxin (Botox), which inhibits acetylcholine secretion in neuron tissue and thereby paralyzes muscle contraction, has been used. However, injection by doctors is required due to its toxicity, and it is prohibited from being used as in cosmetics. Therefore, extensive studies have been made on cosmetics derived from natural plants that can replace Botox and guarantee safety to skin.

Therefore, the present inventors have studied the development of cosmetic materials derived from natural plants not inducing any side effect to skin and having excellent effects in skin aging prevention and skin wrinkle improvement, and have found that a skin-aging cosmetic composition having excellent effects in skin aging prevention and skin wrinkle improvement can be made by containing *Hibiscus esculentus* extracts, which improve skin wrinkles by inhibiting muscle contraction and removing oxygen free radicals, and active ingredients selected from oleanolic acid, ursolic acid, glycyrrhetinic acid and retinol, which improve skin wrinkles generated by aging.

The *Hibiscus esculentus* extracts can comprise oligopeptides extracted from *Hibiscus esculentus* and processed, as active ingredients.

The object of the present invention is to provide an anti-aging cosmetic composition having excellent skin safety and excellent effects in skin aging prevention and skin wrinkle improvement.

DISCLOSURE OF INVENTION

To attain the above object, there is provided an anti-aging cosmetic composition containing *Hibiscus esculentus* extracts and at least one selected from the group consisting of oleanolic acid, ursolic acid, glycyrhetinic acid and retinol.

The *Hibiscus esculentus* extracts are obtained by methods known in the art, for example, leafs, seeds and roots of *Hibiscus esculentus*, which come under the category of mellow flowers, are dried, pulverized and extracted by using water or organic solvent. The organic solvent can be polar solvent such as ethanol, butanol or acetone, or non-polar solvent such as ether, hexane, benzene, chloroform or ethyl acetate, or a mixture thereof.

The *Hibiscus esculentus* extracts may contain oligopeptides extracted from *Hibiscus esculentus* and processed, as active ingredients. The oligopeptides complex according to the present invention removes oxygen free radicals that reduce the function of bio-molecules contributing to skin elasticity, and thereby protects skin from biological oxidation reaction. In addition, it can improve skin wrinkle by increasing collagen synthesis in skin, which leads to an increase of elasticity fiber in the skin derma. Further, it has effects on muscle contraction inhibition or muscle relaxation. In particular, muscle relaxation effects appear in facial expression muscle, which is used when people make a facial expression such as smiling or frowning, and the oligopeptides complex can decrease contractile force of expression muscle, thereby alleviating skin wrinkle temporarily produced at the time of making a facial expression, and preventing the fixation of such temporary skin wrinkle.

In addition, the oligopeptides complex is a mixture of low molecular oligopeptides whose average molecular weight is 262 Da (Dalton), and the content of the oligopeptides complex is preferably 0.00001~10 wt % based on the total weight of the composition. If the content is less than 0.00001 wt %, skin wrinkle improvement effect is insignificant, and if the content is more than 10 wt %, the efficacy does not significantly increase, thus the efficiency of the material is low.

The oleanolic acid, ursolic acid, glycyrhetinic acid and retinol are each preferably contained in an amount of 0.00001~10 wt % based on the total weight of the composition. If the content is less than 0.00001 wt %, skin wrinkle improvement effect is insignificant, and if the content is more than 10 wt %, the efficacy does not significantly increase, thus the efficiency of the material is low.

The formulation of the cosmetic composition in the present invention is not limited to a specific kind. It may be formulated into skin softeners, nutrient toilet water, massage creams, nutrient creams, gels, packs or skin-adhesive type formulations.

BEST MODE FOR CARRYING OUT THE INVENTION

Figure 1:
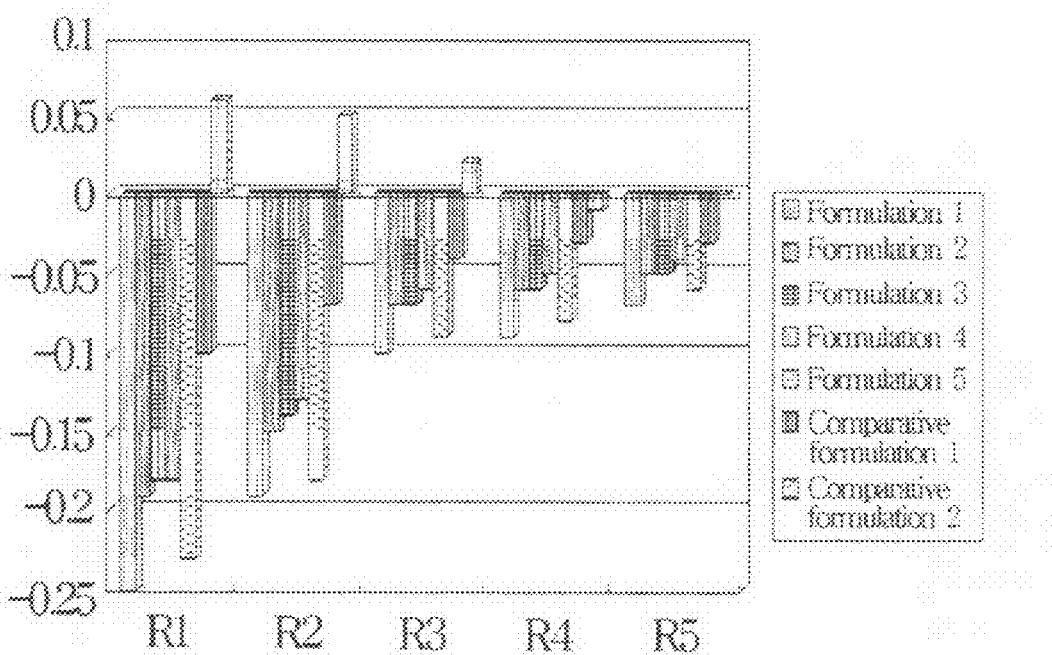
FIG. 1 is a graph showing skin wrinkle improvement of Formulation Examples 1-5 and Comparative Formulation Examples 1 and 2.

The present invention will be described in more detail by way of the following examples. However, these examples are provided for the purpose of illustration only and should not be construed as limiting the scope of the invention, which will be apparent to one skilled in the art.

Experimental Example 1

Effect on Promoting Collagen Synthesis

Human fibroblast was cultured in 24-well microplates, and the culture medium thereof was changed to one containing *Hibiscus esculentus* extracts at concentrations of 0, 1, 5 and 10 ppm, respectively. The *Hibiscus esculentus* extracts used were commercially available oligopeptides obtained from the extracts of *Hibiscus esculentus*, whose product name is MYOXINOL (INCI name: Hydrolyzed *Hibiscus esculentus* Extract: Manufactured by Laboratoires Sérobiologiques). At 3 days of cultivation, 0.5 ml of DMEM culture medium containing 10% FBS was added to each well, then 10 µCi of L[2,3,4,5-3H]-proline was added thereto. 24 hours later, the culture medium and the cells contained in each well were raked, and put into the 5% TCA (Trichloroacetic acid) solution. Each sample was then divided into 2 test tubes, and 1 unit/µl of type I collagenase was added to one of each pair of the test tubes, and cultured at 37° C. for 90 minutes. The other test tube of each pair was stored at 4° C. 0.05 ml of 50% TCA was then added to every test tube, and the test tubes were left at 4° C. for 20 minutes, then each was centrifuged at 12,000 rpm for 10 minutes. Each supernatant and sediment was treated with Liquid Scintillation Counter (LSC) to obtain a CPM (Count Per Minute) value, then Relative Collagen Biosynthesis value (RCB) of control and experimental group was obtained based on the below Numerical Formula 1. The results are shown in Table 1.

$$RCB(\%) = (cpm\ of\ collagen) / \{(cpm\ of\ total\ collagen) \times 5.4 + cpm\ of\ collagen)\} \times 100 \quad \text{[Numerical Formula 1]}$$

TABLE 1

| Concentration of *Hibiscus esculentus* extracts (ppm) | Relative collagen biosynthesis value (RCB) (%) |
|---|---|
| 10 | 140 |
| 5 | 122 |
| 1 | 112 |
| 0 (Control) | 100 |

As can be seen in the above Table 1, *Hibiscus esculentus* Extracts increased the collagen biosynthesis value of fibroblast in a concentration-dependent manner.

Experimental Example 2

Effect on Muscle Relaxation

Sprague-Dawley rats were bled to death, then their diaphragm and phrenic nerves were excised. The tissue slices thereof were put into organ chambers, and the chambers were linked to a force displacement transducer (Grass Co.). 2 kg of tension was applied thereto and electrostimulation was applied for 0.2 msec at intervals of 20 sec at a voltage by which maximum contraction can be shown. 60 minutes later, whether the contraction of diaphragm was constant was checked, and 0, 50, 500, 1000 and 2000 ppm of *Hibiscus esculentus* Extracts were added to the organ chambers to estimate the effect on inhibiting the contraction of diaphragm. The *Hibiscus esculentus* extracts used were commercially available oligopeptides obtained from the extracts of *Hibiscus esculentus*, whose product name is MYOXINOL (INCI name: Hydrolyzed *Hibiscus esculentus* Extract: Manufactured by Laboratoires Sérobiologiques).

TABLE 2

| Concentration of *Hibiscus esculentus* extracts (ppm) | Ratio of inhibiting diaphragm contraction (%) |
|---|---|
| 0 (control) | 0 |
| 50 | 4.0 |
| 500 | 17.9 |
| 1000 | 21.8 |
| 2000 | 30.7 |

As can be seen in the above Table 2; *Hibiscus esculentus* Extracts according to the present invention inhibited diaphragm contraction in a concentration-dependent manner, which means that *Hibiscus esculentus* Extracts have muscle relaxation effects.

Formulation Examples 1-5 and Comparative Formulation Examples 1-2

To estimate the skin wrinkle alleviation effect, cream formulations were prepared in the following compositions shown in Table 3 by a conventional method.

TABLE 3

| Materials | Formulation Example | | | | | Comparative Formulation Example | |
|---|---|---|---|---|---|---|---|
| | 1 | 2 | 3 | 4 | 5 | 1 | 2 |
| *Hibiscus Esculentus* Extracts | 0.01 | 0.01 | 0.01 | 0.01 | 0.01 | 0.01 | — |
| Oleanolic acid | 0.10 | 0.10 | — | — | — | — | — |
| Ursolic acid | 0.10 | — | 0.10 | — | — | — | — |
| Glycyrrhetic acid | 0.10 | — | — | 0.10 | — | — | — |
| Retinol | 0.01 | — | — | — | 0.01 | — | — |
| EDTA-2Na | 0.02 | 0.02 | 0.02 | 0.02 | 0.02 | 0.02 | 0.02 |
| Glycerine | 5.00 | 5.00 | 5.00 | 5.00 | 5.00 | 5.00 | 5.00 |
| Butylene Glycol | 5.00 | 5.00 | 5.00 | 5.00 | 5.00 | 5.00 | 5.00 |
| Vegetable Hydrogenated Oil | 1.50 | 1.50 | 1.50 | 1.50 | 1.50 | 1.50 | 1.50 |
| Stearic acid | 0.60 | 0.60 | 0.60 | 0.60 | 0.60 | 0.60 | 0.60 |
| Glyceryl stearate | 1.00 | 1.00 | 1.00 | 1.00 | 1.00 | 1.00 | 1.00 |
| Cetearyl alcohol | 2.00 | 2.00 | 2.00 | 2.00 | 2.00 | 2.00 | 2.00 |
| Arachidyl/Behenyl Alcohol & arachidyl glucoside | 1.00 | 1.00 | 1.00 | 1.00 | 1.00 | 1.00 | 1.00 |
| Cetyl aryl alcohol & cetearyl glucoside | 2.00 | 2.00 | 2.00 | 2.00 | 2.00 | 2.00 | 2.00 |
| Liquid paraffin | 6.00 | 6.00 | 6.00 | 6.00 | 6.00 | 6.00 | 6.00 |
| Caprilic/carlic triglyceride | 6.00 | 6.00 | 6.00 | 6.00 | 6.00 | 6.00 | 6.00 |
| Carbomer | 0.05 | 0.05 | 0.05 | 0.05 | 0.05 | 0.05 | 0.05 |
| Triethanol amine (TEA) | 0.05 | 0.05 | 0.05 | 0.05 | 0.05 | 0.05 | 0.05 |
| Preservative, Perfume, pigment | q.s. | q.s. | q.s. | q.s. | q.s. | q.s. | q.s. |
| Distilled water | To 100 | To 100 | To 100 | To 100 | To 100 | To 100 | To 100 |

The *Hibiscus esculentus* extracts used were commercially available oligopeptides obtained from the extracts of *Hibiscus esculentus*, whose product name is MYOXINOL (INCI name: Hydrolyzed *Hibiscus esculentus* Extract: Manufactured by Laboratoires Sérobiologiques).

Experimental Example 3

Improvement of Skin Wrinkle

The following was performed to identify the effects of the above formulations in Table 3 on the improvement of skin wrinkle. 140 women aged 30-39 were divided into 7 groups (20 people per group). To each group, one of the formulations 1, 2, 3, 4, 5, comparative formulations 1 and 2 was applied twice per day for 8 weeks, and replicas were prepared after 8 weeks using silicon. The state of skin wrinkles was image analyzed by visiometer (SV600, Courage+Khazaka Electronic GmbH, Germany). The average of the values obtained by subtracting each parameter value before the application from the same person's corresponding parameter value 8 weeks later are shown in Table 4.

TABLE 4

| Clinical result 8 weeks after use | R1 | R2 | R3 | R4 | R5 |
|---|---|---|---|---|---|
| Formulation 1 | −0.25 | −0.19 | −0.1 | −0.09 | −0.07 |
| Formulation 2 | −0.19 | −0.16 | −0.07 | −0.06 | −0.05 |
| Formulation 3 | −0.18 | −0.14 | −0.07 | −0.06 | −0.05 |
| Formulation 4 | −0.18 | −0.13 | −0.06 | −0.05 | −0.04 |
| Formulation 5 | −0.23 | −0.18 | −0.09 | −0.08 | −0.06 |
| Comparative Formulation 1 | −0.10 | −0.07 | −0.04 | −0.03 | −0.03 |
| Comparative Formulation 2 | 0.06 | 0.05 | 0.02 | −0.01 | 0.00 |

R1: Difference between the maximum value and the minimum value of skin wrinkle contour
R2: Average of R1 obtained by the difference between the value of an arbitrary contour and the value of the fifth contour from the arbitrary contour
R3: Maximum of R1 obtained by the difference between the value of an arbitrary contour and the value of the fifth contour from the arbitrary contour
R4: Average of each peak-to-peak value at the baseline of wrinkle contour
R5: Difference between the baseline and the value of each wrinkle contour As can be seen in Table 4 and FIG. 1, the formulations 1~5, which contain *Hibiscus esculentus* extracts and at least one selected from the group consisting of oleanolic acid, ursolic acid, glycyrhetinic acid and retinol, are superior in improvement of skin wrinkle to the comparative formulations 1 and 2, and especially the effect of formulation 1 was excellent.

In addition, from the safety test of the above formulations 1~5 and the comparative formulations 1~2, it was recognized that the cosmetic composition of the present invention shows excellent safety.

INDUSTRIAL APPLICATION OF THE INVENTION

As above described, the cosmetic composition according to the present invention shows excellent safety to skin and skin wrinkle improvement. Therefore, it can be used in a composition for external application having anti-skin aging efficacy.

The invention claimed is:
1. A method of combating skin aging effects comprising topically applying to the skin of a subject in need thereof a composition consisting of an extract of *Hibiscus esculentus*, oleanolic acid, ursolic acid, glycyrrhetinic acid and retinol.

2. A method of improving skin elasticity comprising topically applying to the skin of a subject in need thereof a composition consisting of an extract of *Hibiscus esculentus*, oleanolic acid, ursolic acid, glycyrrhetinic acid and retinol.

3. A method of improving skin contraction comprising topically applying to the skin of a subject in need thereof a composition consisting of an extract of *Hibiscus esculentus*, oleanolic acid, ursolic acid, glycyrrhetinic acid and retinol.

4. A method of combating the formation of skin wrinkles comprising topically applying to the skin of a subject in need thereof a composition consisting of an extract of *Hibiscus esculentus*, oleanolic acid, ursolic acid, glycyrrhetinic acid and retinol.

* * * * *